US010835221B2

(12) United States Patent
Sheps et al.

(10) Patent No.: US 10,835,221 B2
(45) Date of Patent: Nov. 17, 2020

(54) IMPLANT-CINCHING DEVICES AND SYSTEMS

(71) Applicant: Valtech Cardio, Ltd., Or Yehuda (IL)

(72) Inventors: Tal Sheps, Givat Shmuel (IL); Yaron Keidar, Haifa (IL); Yuval Zipory, Modi'in (IL); Brian S. Conklin, Orange, CA (US)

(73) Assignee: Valtech Cardio, Ltd., Or Yehuda (IL)

( * ) Notice: Subject to any disclaimer, the term of this patent is extended or adjusted under 35 U.S.C. 154(b) by 227 days.

(21) Appl. No.: 16/154,233

(22) Filed: Oct. 8, 2018

(65) Prior Publication Data
US 2019/0125325 A1     May 2, 2019

Related U.S. Application Data

(60) Provisional application No. 62/580,646, filed on Nov. 2, 2017.

(51) Int. Cl.
*A61B 17/00*     (2006.01)
*A61B 17/12*     (2006.01)
(Continued)

(52) U.S. Cl.
CPC .... *A61B 17/00234* (2013.01); *A61B 17/0057* (2013.01); *A61B 17/12013* (2013.01);
(Continued)

(58) Field of Classification Search
CPC .... A61B 17/00234; A61B 2017/00243; A61B 17/12009; A61B 17/12013;
(Continued)

(56) References Cited

U.S. PATENT DOCUMENTS 3,604,488 A     9/1971     Wishart et al.
3,656,185 A     4/1972     Carpentier
(Continued)

FOREIGN PATENT DOCUMENTS

EP     1034753 A1     9/2000
WO     9205093 A1     4/1992
(Continued)

OTHER PUBLICATIONS

Agarwal et al. International Cardiology Perspective Functional Tricuspid Regurgitation, Circ Cardiovasc Interv 2009;2;2;565-573 (2009).
(Continued)

*Primary Examiner* — Wade Miles
(74) *Attorney, Agent, or Firm* — Thomas C. Richardson

(57) ABSTRACT

An implant having an implant body, a gripper, an elastic pouch, and an elongate member. The pouch can be coupled to the gripper, can have a first part and a second part, can have a contracted state toward which the pouch is elastically biased, and can be reversibly stretchable into a stretched state. The elongate member can have a first end portion coupled to the implant body, a second end portion fastened to the second part of the pouch, and a mid-portion extending (i) from the second end portion, through the pouch to the first part of the pouch, and (ii) out of the pouch to the first end portion. In at least one state of the gripper, the mid-portion can be slidable through the gripper and into the pouch. Other embodiments are also described.

19 Claims, 7 Drawing Sheets

(51) Int. Cl.
  *A61F 2/24* (2006.01)
  *A61B 17/04* (2006.01)
  *A61B 17/068* (2006.01)
  *A61B 17/064* (2006.01)
  *A61F 2/95* (2013.01)

(52) U.S. Cl.
  CPC .......... *A61F 2/2445* (2013.01); *A61B 17/068* (2013.01); *A61B 2017/00243* (2013.01); *A61B 2017/0496* (2013.01); *A61B 2017/0649* (2013.01); *A61F 2/2478* (2013.01); *A61F 2/9517* (2020.05); *A61F 2210/0057* (2013.01); *A61F 2220/0016* (2013.01); *A61F 2250/001* (2013.01); *A61F 2250/0007* (2013.01)

(58) Field of Classification Search
  CPC ........... A61B 2017/12018; A61B 2017/00287; A61B 17/221; A61B 2017/2212; A61B 2017/15; A61B 17/132; A61B 17/1322; A61B 17/1325; A61B 17/1327; A61F 2/2445; A61F 2/2448; A61F 2/2478; A61F 2/2481; A61F 2/2487; A61F 2002/249; A61F 2/958; A61F 2002/9583; A61F 2002/9586
  See application file for complete search history.

(56) References Cited

U.S. PATENT DOCUMENTS

| | | |
|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,593,424 A | 1/1997 | Northrup, III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,782,844 A | 7/1998 | Yoon et al. |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |

(56) References Cited

U.S. PATENT DOCUMENTS

| | | |
|---|---|---|
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langherg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,121 B2 | 5/2004 | Ortiz et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,964,684 B2 | 11/2005 | Ortiz et al. |
| 6,964,686 B2 | 11/2005 | Gordon |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,087,064 B1 | 6/2006 | Hyde |
| 7,077,850 B2 | 7/2006 | Kortenbach |
| 7,077,862 B2 | 7/2006 | Vidlund et al. |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Weber et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,683,538 B2 | 3/2010 | Yoo et al. |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,780,726 B2 | 6/2010 | Seguin |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,871,368 B2 | 1/2011 | Zollinger et al. |
| 7,871,433 B2 | 1/2011 | Lattouf |
| 7,883,475 B2 | 2/2011 | Dupont et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,992,567 B2 | 8/2011 | Hirotstika et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |

(56) References Cited

U.S. PATENT DOCUMENTS

| | | |
|---|---|---|
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,693,865 B2 | 7/2017 | Gilmore et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0171760 A1 | 9/2003 | Gambale |
| 2003/0199974 A1 | 10/2003 | Lee et al. |
| 2003/0204195 A1 | 10/2003 | Keane et al. |
| 2003/0229350 A1 | 12/2003 | Kay |
| 2003/0229395 A1 | 12/2003 | Cox |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0059413 A1 | 3/2004 | Argento |
| 2004/0122514 A1 | 6/2004 | Fogarty et al. |
| 2004/0127982 A1 | 7/2004 | Machold et al. |

(56) References Cited

U.S. PATENT DOCUMENTS

| | | |
|---|---|---|
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0243227 A1 | 12/2004 | Starksen et al. |
| 2004/0260317 A1 | 12/2004 | Bloom et al. |
| 2004/0260393 A1 | 12/2004 | Randert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0177228 A1 | 6/2005 | Solem et al. |
| 2005/0159728 A1 | 7/2005 | Armour et al. |
| 2005/0171601 A1 | 8/2005 | Cosgrove et al. |
| 2005/0177180 A1 | 8/2005 | Kaganov et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0184240 A1 | 6/2006 | Jimenez et al. |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086203 A1 | 4/2008 | Roberts |
| 2008/0091257 A1 | 4/2008 | Andreas et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |

(56) References Cited

U.S. PATENT DOCUMENTS

| | | |
|---|---|---|
| 2008/0281411 A1 | 11/2008 | Berreklouw |
| 2008/0288044 A1 | 11/2008 | Osborne |
| 2008/0288062 A1 | 11/2008 | Andrieu et al. |
| 2008/0300537 A1 | 12/2008 | Bowman |
| 2008/0300629 A1 | 12/2008 | Surti |
| 2009/0028670 A1 | 1/2009 | Garcia et al. |
| 2009/0043381 A1 | 2/2009 | Macoviak et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0088837 A1 | 4/2009 | Gillinov et al. |
| 2009/0093677 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130992 A1 | 5/2010 | Machold et al. |
| 2010/0152845 A1 | 6/2010 | Bloom et al. |
| 2010/0161043 A1 | 6/2010 | Maisano et al. |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0286628 A1 | 11/2010 | Gross |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0118832 A1 | 5/2011 | Punjabi |
| 2011/0137410 A1 | 6/2011 | Hacohen |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0095552 A1 | 4/2012 | Spence et al. |
| 2012/0109155 A1 | 5/2012 | Robinson et al. |
| 2012/0150290 A1 | 6/2012 | Gabbay |
| 2012/0158021 A1 | 6/2012 | Morrill |
| 2012/0179086 A1 | 7/2012 | Shank et al. |
| 2012/0191182 A1 | 7/2012 | Hauser et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0296349 A1 | 11/2012 | Smith et al. |
| 2012/0296417 A1 | 11/2012 | Hill |
| 2012/0310330 A1 | 12/2012 | Buchbinder et al. |
| 2012/0323313 A1 | 12/2012 | Seguin |
| 2013/0030522 A1 | 1/2013 | Rowe et al. |
| 2013/0046373 A1 | 2/2013 | Cartledge et al. |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0268069 A1 | 10/2013 | Zakai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2014/0081394 A1 | 3/2014 | Keranen et al. |
| 2014/0088368 A1 | 3/2014 | Park |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meter et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheds et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0081006 A1* | 3/2015 | Chuter .............. A61F 2/958 623/1.11 |
| 2015/0081014 A1 | 3/2015 | Gross et al. |

(56) References Cited

U.S. PATENT DOCUMENTS

| | | | |
|---|---|---|---|
| 2015/0112432 | A1 | 4/2015 | Reich et al. |
| 2015/0127097 | A1 | 5/2015 | Neumann et al. |
| 2015/0182336 | A1 | 7/2015 | Zipory et al. |
| 2015/0272586 | A1 | 10/2015 | Herman et al. |
| 2015/0272734 | A1 | 10/2015 | Sheps et al. |
| 2015/0282931 | A1 | 10/2015 | Brunnett et al. |
| 2016/0008130 | A1 | 1/2016 | Hasin |
| 2016/0008132 | A1 | 1/2016 | Cabiri et al. |
| 2016/0058557 | A1 | 3/2016 | Reich et al. |
| 2016/0113767 | A1 | 4/2016 | Miller et al. |
| 2016/0120645 | A1 | 5/2016 | Alon |
| 2016/0135953 | A1 | 5/2016 | Alon et al. |
| 2016/0158008 | A1 | 6/2016 | Miller et al. |
| 2016/0242762 | A1 | 8/2016 | Gilmore et al. |
| 2016/0262755 | A1 | 9/2016 | Zipory et al. |
| 2016/0302917 | A1 | 10/2016 | Schewel |
| 2016/0317302 | A1 | 11/2016 | Madjarov et al. |
| 2016/0361058 | A1 | 12/2016 | Bolduc et al. |
| 2016/0361168 | A1 | 12/2016 | Gross et al. |
| 2016/0361169 | A1 | 12/2016 | Gross et al. |
| 2017/0000609 | A1 | 1/2017 | Gross et al. |
| 2017/0216066 | A1* | 8/2017 | Bar .................. A61F 2/91 |
| 2017/0224489 | A1 | 8/2017 | Starksen et al. |
| 2017/0245993 | A1 | 8/2017 | Gross et al. |
| 2018/0049875 | A1 | 2/2018 | Iflah et al. |
| 2019/0125325 | A1* | 5/2019 | Sheps .............. A61B 17/00234 |

FOREIGN PATENT DOCUMENTS

| | | | |
|---|---|---|---|
| WO | 9846149 | A1 | 10/1998 |
| WO | 02085250 | A3 | 2/2003 |
| WO | 03047467 | A1 | 6/2003 |
| WO | 201000454 | A1 | 1/2010 |
| WO | 2012176195 | A3 | 3/2013 |
| WO | 2014064964 | A1 | 5/2014 |

OTHER PUBLICATIONS

Ahmadi, A., G. Spillner, and Th Johannesson. "Hemodynamic changes following experimental production and correction of acute mitral regurgitation with an adjustable ring prosthesis," The Thoracic and cardiovascular surgeon36.06 (1988): 313-319.

Ahmadi, Ali et al. "Percutaneously adjustable pulmonary artery band." The Annals of thoracic surgery 60 (1995): S520-S522.

Alfieri et al., "An effective technique to correct anterior mitral leaflet prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

Alfieri et al., "The edge to edge technique," The European Association for Cardio-Thoracic Surgery 14th Annual Meeting Oct. 7-11, Book of Procees. (2000).

Alfieri et al. "Novel Suture Device for Beating-Heart Mitral Leaflet Approximation", Ann Thorac Surg. 2002, 74:1488-1493.

Alfieri, "The edge-to-edge repair of the mitral valve," [Abstract] 6th Annual NewEra Cardiac Care: Innovation & Technology, Heart Surgery Forum pp. 103, (2000).

Amplatzer Cardiac Plug brochure (English pages), AGA Medical Corporation (Plymouth, MN) (copyright 2008-2010, downloaded Jan. 11, 2011).

AMPLATZER® Cribriforrn Occluder. A patient guide to Percutaneous, Transcatheter, Atrial Septal Defect Closuer, AGA Medical Corporation, Apr. 2008.

AMPLATZER® Septal Occluder. A patient guide to the Non-Surgical Closuer of the Atrial Septal Defect Using the AMPLATZER Septal Occluder System, AGA Medical Corporation, Apr. 2008.

Assad, Renato S. "Adjustable Pulmonary Artery Banding." (2014).

Brennan, Jennifer, 510(k) Summary of safety and effectiveness, Jan. 2008.

Daebritz, S. et al. "Experience with an adjustable pulmonary artery banding device in two cases: initial success-midterm failure." The Thoracic and cardiovascular surgeon 47.01 (1999): 51-52.

Dang NC et al. "Simplified Placement of Multiple Artificial Mitral Valve Chords," The Heart Surgery Forum #2005-1005, 8 (3) (2005).

Dictionary.com definition of "lock", Jul. 29, 2013.

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

Elliott, Daniel S., Gerald W. Timm, and David M. Barrett. "An implantable mechanical urinary sphincter: a new nonhydraulic design concept." Urology52.6 (1998): 1151-1154.

Langer et al. Ring plus String: Papillary muscle repositioning as an adjunctive repair technique for ischemic mitral regurgitation, The Journal of Thoracic Cardiovascular surgery vol. 133 No. 1, Jan. 2007.

Langer et al. RING+STRING, Successful Repair technique for ischemic mitral regurgitation with severe leaflet Tethering, The Department of Thoracic Cardiovascular surgery, Hamburg, Germany, Nov. 2008.

Maisano, "The double-orifice technique as a standardized approach to treat mitral," European Journal of Cardio-thoracic Surgery 17 (2000) 201-205.

Odell JA et al., "Early Results of a Simplified Method of Mitral Valve Annuloplasty," Circulation 92:150-154 (1995).

O'Reilly S et al., "Heart valve surgery pushes the envelope," Medtech Insight 8(3): 73, 99-108 (2006).

Park, Sang C. et al. "A percutaneously adjustable device for banding of the pulmonary trunk." International journal of cardiology 9.4 (1985): 477-484.

Swain CP et al., "An endoscopically deliverable tissue-transfixing device for securing biosensors in the gastrointestinal tract," Gastrointestinal Endoscopy 40(6): 730-734 (1994).

Swenson, O. An experimental implantable urinary sphincter. Invest Urol. Sep. 1975;14(2):100-3.

Swenson, O. and Malinin, T.I., 1978. An improved mechanical device for control of urinary incontinence. investigative urology, 15(5), pp. 389-391.

Swenson, Orvar. "Internal device for control of urinary incontinence." Journal of pediatric surgery 7.5 (1972): 542-545.

Tajik, Abdul, "Two dimensional real-time ultrasonic imaging of the heart and great vessels", Mayo Clin Proc. vol. 53:271-303, 1978.

\* cited by examiner

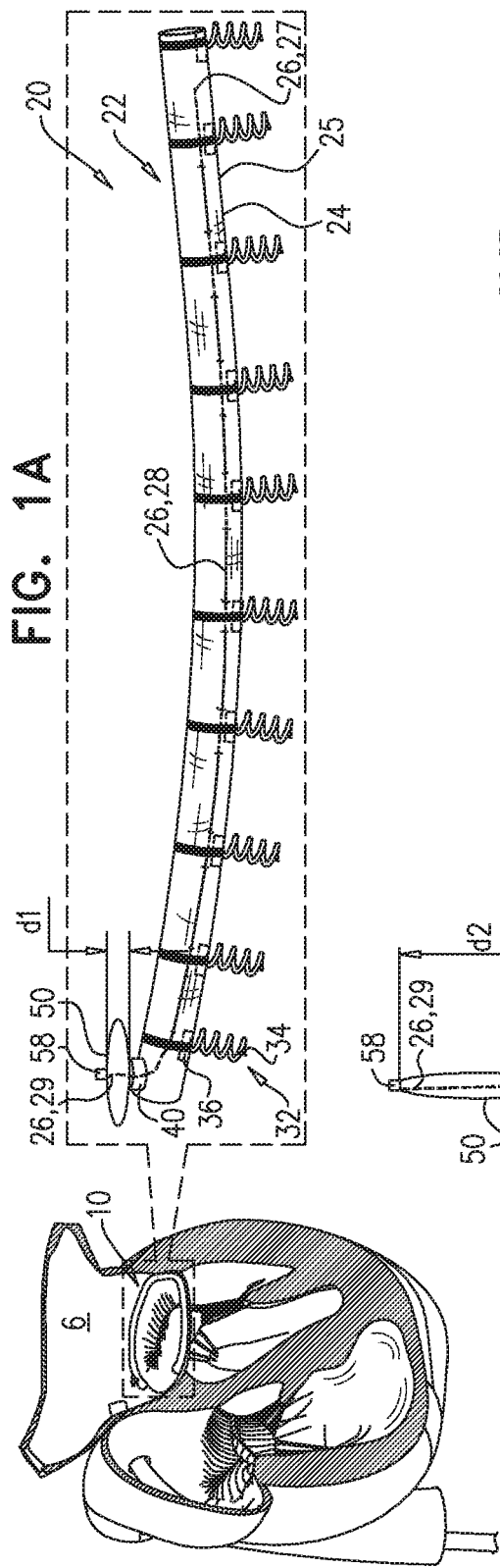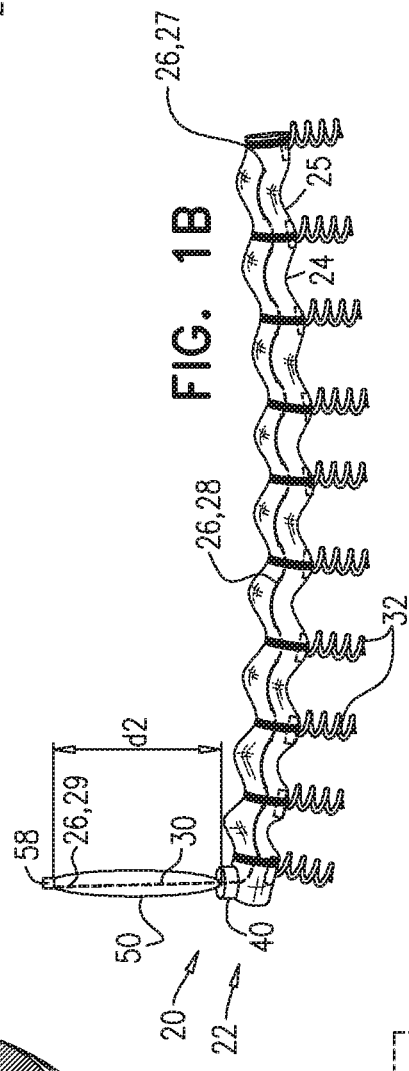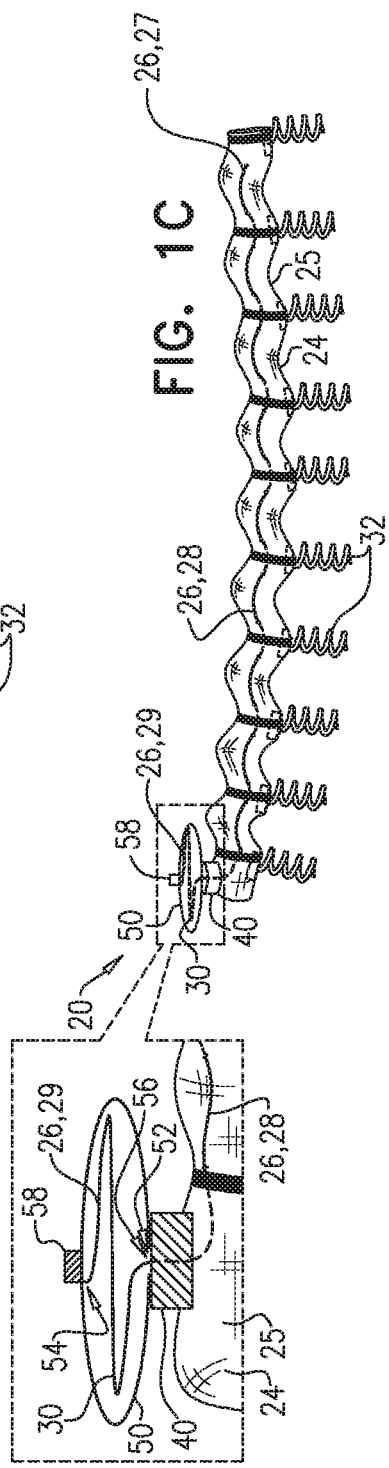

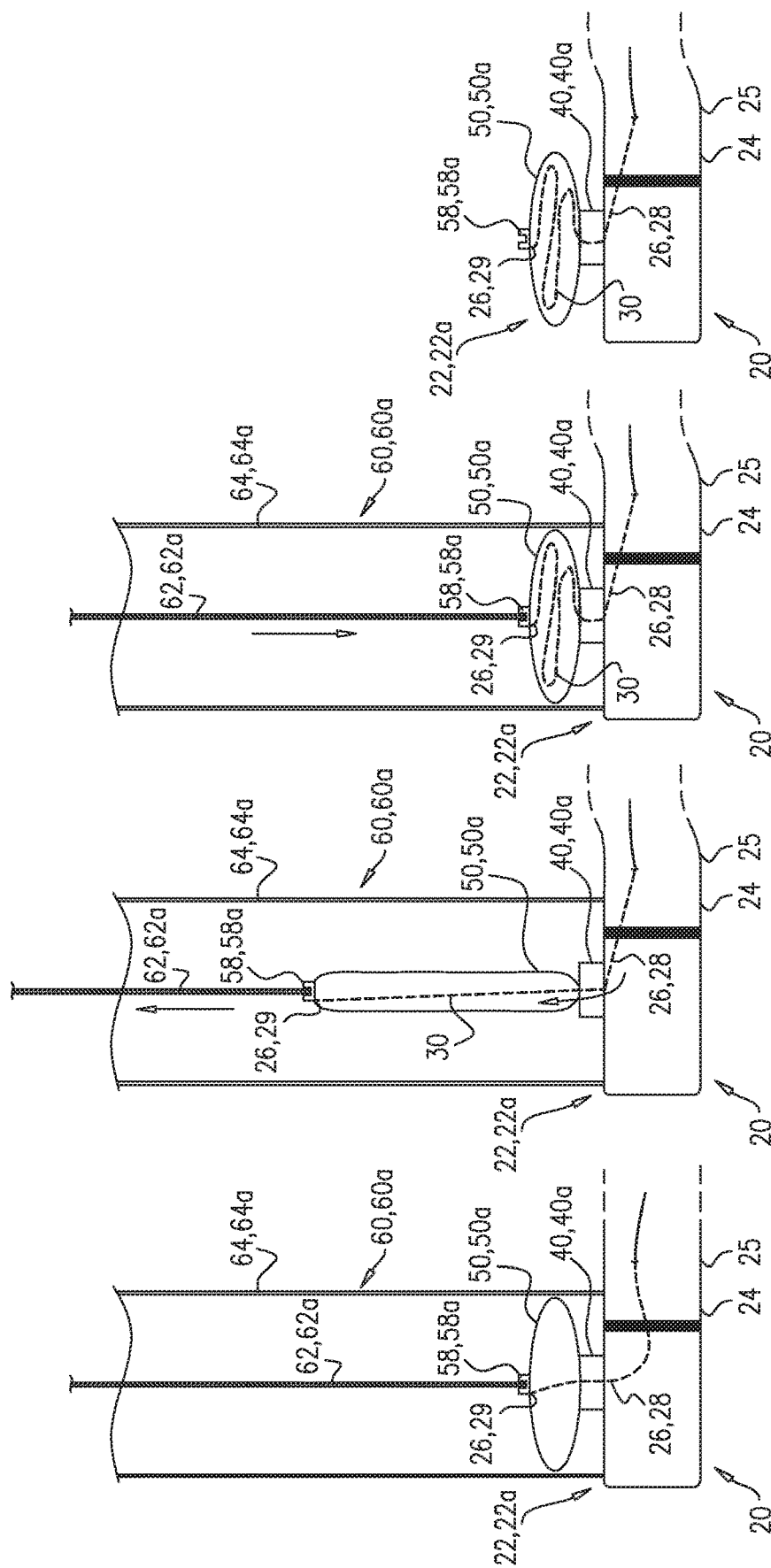

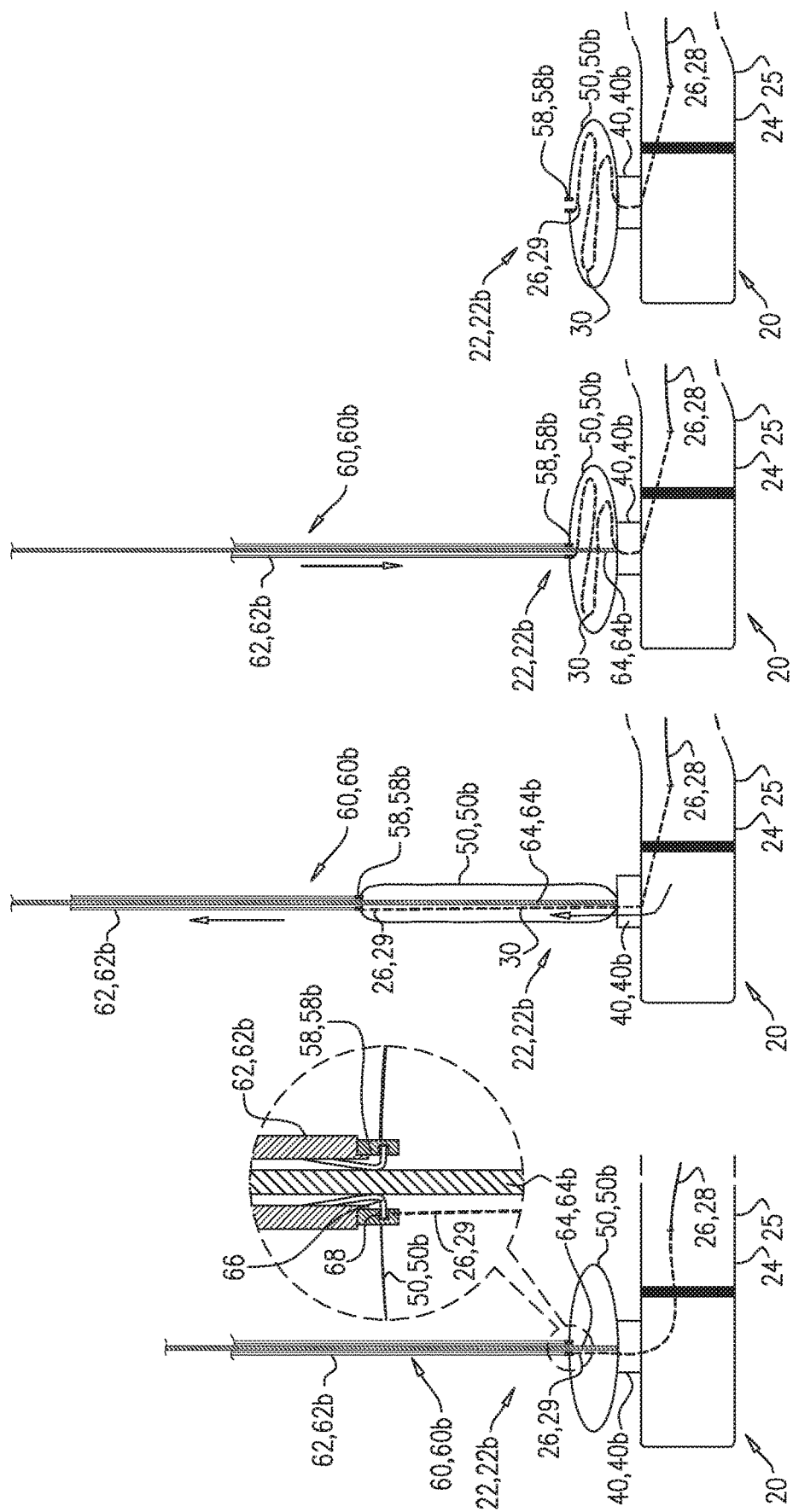

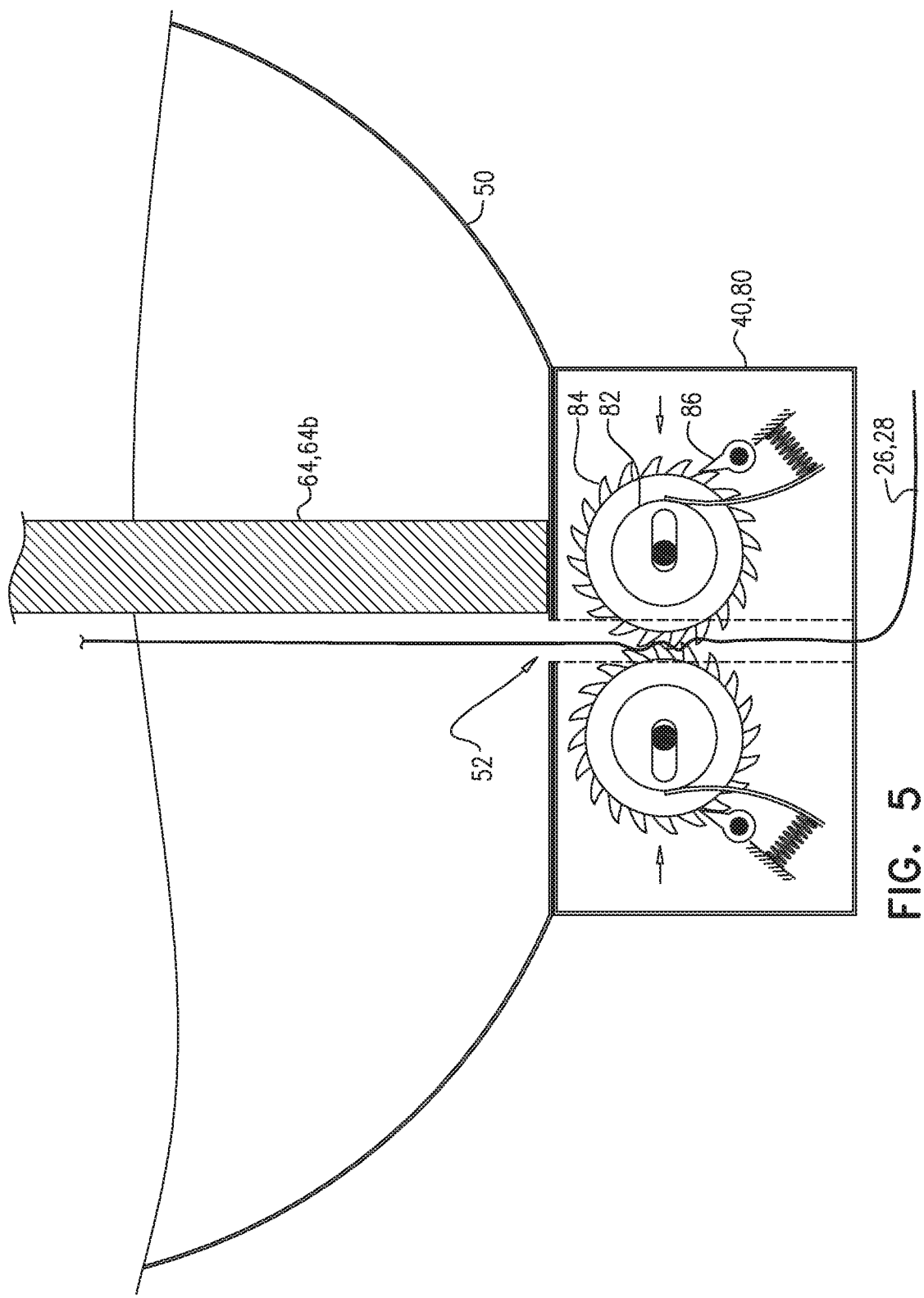

IMPLANT-CINCHING DEVICES AND SYSTEMS

CROSS-REFERENCES TO RELATED APPLICATIONS

The present application claims priority from U.S. Provisional application 62/580,646 to Sheps et al., filed Nov. 2, 2017, and entitled "Implant-cinching devices and systems," which is incorporated herein by reference.

FIELD OF THE INVENTION

Some applications of the present invention relate in general to adjustment of an implant. For example, some applications of the present invention relate to contraction of a cardiovascular implant.

BACKGROUND

Ischemic heart disease can cause valve regurgitation, such as mitral regurgitation by the combination of ischemic dysfunction of the papillary muscles, and the dilatation of the left ventricle that is present in ischemic heart disease, with the displacement of the papillary muscles and the dilatation of the mitral valve annulus.

Dilation of the annulus of the mitral valve (or another valve) can prevent the valve leaflets from fully coapting when the valve is closed. Mitral regurgitation of blood from the left ventricle into the left atrium results in increased total stroke volume and decreased cardiac output, and ultimate weakening of the left ventricle secondary to a volume overload and a pressure overload of the left atrium.

Dilation of other regions of the heart, vascular system, and/or other valve annuluses can also result in similar problems, including regurgitation at other valves.

Annuloplasty, such as by implantation of an annuloplasty ring or other annuloplasty device, can be used to improve leaflet coaptation by adjusting the shape of a native valve annulus, e.g., the mitral annulus, tricuspid annulus, etc.

SUMMARY OF THE INVENTION

This summary is meant to provide some examples and is not intended to be limiting of the scope of the invention in any way. For example, any feature included in an example of this summary is not required by the claims, unless the claims explicitly recite the features. Also, the features described can be combined in a variety of ways. The description herein relates to systems, assemblies, methods, devices, apparatuses, combinations, etc. that may be utilized for cinching, tightening, tensioning a medical implant. Various features and steps as described elsewhere in this disclosure may be included in the examples summarized here.

As one example, an adjustment system can include an elongate member. The elongate member can enter into a pouch (e.g., an elastic pouch) at a first part of the pouch, extend through the pouch, and can be connected to a second part of the pouch. The system and its components can be configured such that stretching of the pouch (e.g., elastically stretching the pouch) causes a distance between the first and second parts of the pouch to increase, thereby drawing more of the elongate member into the pouch. The system can include a gripper. The gripper can be disposed at the first part of the pouch, and can be configured such that it can inhibit the elongate member from re-exiting the pouch when the pouch is allowed to re-contract. Therefore, the net result of stretching and releasing the pouch can be reduction of a length of the elongate member that is disposed outside of the pouch.

The elongate member can be attached to or be part of an implant or implant body in a manner that changes a dimension of the implant or implant body when the length of the elongate member that is disposed outside of the pouch is reduced. For some applications, the implant or implant body includes a sleeve that is longitudinally contracted when the length of the elongate member that is disposed outside of the pouch is reduced. For some such applications, the implant or implant body can be an annuloplasty ring structure, other annuloplasty device structure, or other cinchable/tensionable structure, anchored to the native valve annulus (e.g., mitral valve annulus, tricuspid valve annulus, etc.), and longitudinal contraction of the sleeve contracts the native valve annulus. The implant or implant body can have an open or closed (e.g., a closed ring) configuration and can be configured for transvascular or transcatheter implantation and/or surgical implantation.

A system or apparatus for tightening, cinching, or tensioning can include one or more of a gripper, an elastic pouch, and an elongate member. The elastic pouch can have a first part and a second part. The first part can be coupled to the gripper. The elastic pouch can be stretchable into a stretched state in which the pouch defines a stretched distance between the first part and the second part. The elastic pouch can also have a contracted state toward which the pouch is elastically biased, and in which the pouch defines a contracted distance between the first part and the second part, the contracted distance being smaller than the stretched distance. In at least one state of the gripper, the elongate member can be slidable through the gripper and into the pouch.

The system or apparatus above and/or another similar system or apparatus can include one or more of an implant having an implant body, a gripper, coupled to the implant body, an elastic pouch, and an elongate member. The elastic pouch can be coupled to the gripper, have a first part and a second part, be reversibly stretchable into a stretched state in which the pouch defines a stretched distance between the first part and the second part, and/or have a contracted state toward which the pouch is elastically biased, and in which the pouch defines a contracted distance between the first part and the second part, the contracted distance being smaller than the stretched distance.

The elongate member can have a first end portion coupled to the implant body, a second end portion fastened to the second part of the pouch, and a third portion or a mid-portion extending (i) from the second end portion, through the pouch to the first part of the pouch, and (ii) out of the pouch to the first end portion. In at least one state of the gripper, the third portion or mid-portion can be slidable through the gripper and into the pouch.

In an application, the implant or implant body can include an annuloplasty ring structure, other annuloplasty device structure, or other cinchable/tensionable structure.

In an application, the gripper includes a plurality of teeth that provide a gripping surface configured to grip the elongate member.

In an application, the pouch is coupled to the gripper by the first part of the pouch being coupled to the gripper.

In an application, the first part of the pouch defines an opening into the pouch, and in the at least one state of the gripper, the third portion or mid-portion in slidable through the gripper and into the pouch via the opening.

In an application, in at least one state of the gripper, the gripper inhibits sliding of the third portion or mid-portion through the gripper and out of the pouch.

In an application, the at least one state of the gripper includes a unidirectional state in which the gripper facilitates sliding of the third portion or mid-portion through the gripper in a first direction that is into the pouch, and inhibits sliding of the third portion or mid-portion through the gripper in a second, opposite direction that is out of the pouch.

In an application, the gripper has an unlocked state in which the gripper facilitates sliding of the third portion or mid-portion through the gripper in the first direction and in the second direction.

In an application, the gripper includes one or more wheels that, in the unidirectional state, grip the third portion or mid-portion, each of the one or more wheels configured to rotate in only one rotational direction.

In an application, the at least one state of the gripper includes:

an unlocked state in which the gripper facilitates sliding of the third portion or mid-portion through the gripper in a first direction that is into the pouch, and in a second, opposite direction that is out of the pouch, and a locked state in which the gripper inhibits sliding of the third portion or mid-portion through the gripper in the first direction and in the second direction.

In an application, the apparatus further includes an unlocker, configured to actuate the gripper to transition between the unlocked state and the locked state.

In an application, the unlocker is configured to maintain the gripper in the unlocked state, the gripper being configured to automatically transition into the locked state upon removal of the unlocker from the gripper.

In an application, the unlocker includes a filament, reversibly coupled to the unlocker, and wherein tensioning of the filament transitions the gripper to the unlocked state.

In an application, the unlocker is configured to reversibly actuate the gripper to transition repeatedly between the unlocked state and the locked state.

In an application, the gripper includes a jaw that, in the locked state, clamps onto the third portion or mid-portion, and the unlocker maintains the gripper in the unlocked state by inhibiting the jaw from clamping onto the third portion or mid-portion.

In an application:

the gripper includes a jaw that, in the locked state, clamps onto the third portion or mid-portion, and the unlocker includes a filament (e.g., a suture or wire), reversibly coupled to the jaw such that tensioning of the filament transitions the gripper into the unlocked state by pulling the jaw away from the third portion or mid-portion.

In an application:

the apparatus further includes a guide member that defines the unlocker at a distal end of the guide member, the apparatus further includes an adjustment-facilitating tool that includes a tensioning element that is reversibly couplable to the pouch, such that while coupled to the pouch, application of a proximally-directed force to the tensioning element stretches the pouch into its stretched state, and the adjustment-facilitating tool is advanceable along the guide member to the implant subsequent to implantation of the implant.

In an application, the apparatus further includes an adjustment-facilitating tool that includes a tensioning element that is reversibly couplable to the pouch, such that while coupled to the pouch, application of a proximally-directed force to the tensioning element stretches the pouch into its stretched state.

In an application, the apparatus further includes a guide member, reversibly coupled to the implant, and the adjustment-facilitating tool is advanceable along the guide member to the implant subsequent to implantation of the implant.

In an application, the adjustment-facilitating tool further includes a pressing element, slidably coupled to the tensioning element such that, while the tensioning element is coupled to the pouch, application of a distally-directed force to the pressing element presses the pressing element against the implant.

In an application, the pressing element maintains coupling between the tensioning element and the pouch, and withdrawal of the pressing element decouples the tensioning element from the pouch.

In an application, the pressing element is disposed coaxially around the tensioning element.

In an application, the tensioning element is disposed coaxially around the pressing element.

In an application, the pressing element is slidably coupled to the tensioning element such that, while the tensioning element is coupled to the pouch, application of the distally-directed force to the pressing element presses the pressing element against the implant body.

In an application, the pressing element is slidably coupled to the tensioning element such that, while the tensioning element is coupled to the pouch, application of the distally-directed force to the pressing element presses the pressing element against the gripper.

In an application, the pressing element is slidably coupled to the tensioning element such that, while the tensioning element is coupled to the pouch, application of the distally-directed force to the pressing element presses the pressing element against an inner surface of the pouch.

In an application, the implant further includes a coupling that is attached to the pouch, and to which the adjustment-facilitating tool is reversibly couplable.

In an application, stretching of the pouch into the stretched state contracts the implant body.

In an application, the implant body includes a fabric sleeve that defines a circumferential wall that defines a lumen, the elongate member extends along the sleeve to where the first end portion of the elongate member is coupled to the sleeve, and stretching of the pouch into the stretched state longitudinally contracts the sleeve.

In an application, the apparatus further includes a plurality of anchors, and each anchor of the plurality of anchors:

includes a tissue-coupling element and a tool-engaging head fastened to one end of the tissue-coupling element, and is configured to be intracorporeally delivered into the lumen of the sleeve, and to anchor the sleeve to the tissue of the subject by the tissue-coupling element being driven through the circumferential wall and into the tissue.

In one embodiment, a system or apparatus can include one or more of an implant, a gripper, an elastic pouch, and an elongate member. The elastic pouch can have a first part and a second part, the first part being coupled to the gripper. The elastic pouch can be reversibly stretchable into a stretched state in which the pouch defines a stretched distance between the first part and the second part. The elastic pouch can have a contracted state toward which the pouch is elastically biased, and in which the pouch defines a contracted distance between the first part and the second part, the contracted distance being smaller than the stretched distance. In at least one state of the gripper, the elongate member is slidable through the gripper and into the pouch. The elongate member can have an end portion that is fastened to the second part of the pouch, such that, in at least the one state of the gripper, stretching of the pouch into the stretched state pulls the elongate member through the gripper and into the pouch.

In an application, the gripper includes a plurality of teeth that provide a gripping surface configured to grip the elongate member.

In an application, the first part of the pouch defines an opening into the pouch, and in the at least one state of the gripper, the elongate member in slidable through the gripper and into the pouch via the opening.

In an application, in at least one state of the gripper, the gripper inhibits sliding of the elongate member through the gripper and out of the pouch.

In an application, the at least one state of the gripper includes a unidirectional state in which the gripper facilitates sliding of the elongate member through the gripper in a first direction that is into the pouch, and inhibits sliding of the elongate member through the gripper in a second, opposite direction that is out of the pouch.

In an application, the gripper has an unlocked state in which the gripper facilitates sliding of the elongate member through the gripper in the first direction and in the second direction.

In an application, the gripper includes one or more wheels that, in the unidirectional state, grip the elongate member, each of the one or more wheels configured to rotate in only one rotational direction.

In an application, the at least one state of the gripper includes:
an unlocked state in which the gripper facilitates sliding of the elongate member through the gripper in a first direction that is into the pouch, and in a second, opposite direction that is out of the pouch, and
a locked state in which the gripper inhibits sliding of the elongate member through the gripper in the first direction and in the second direction.

In an application, the apparatus further includes an unlocker, configured to maintain the gripper in the unlocked state, the gripper configured to automatically transition into the locked state upon removal of the unlocker from the gripper.

In an application, the gripper includes a jaw that, in the locked state, clamps onto the elongate member, and the unlocker maintains the gripper in the unlocked state by inhibiting the jaw from clamping onto the elongate member.

In an application:
the apparatus further includes a guide member that defines the unlocker at a distal end of the guide member,
the apparatus further includes an adjustment-facilitating tool that includes a tensioning element that is reversibly couplable to the pouch, such that while coupled to the pouch, application of a proximally-directed force to the tensioning element stretches the pouch into its stretched state, and
the adjustment-facilitating tool is advanceable along the guide member to the implant subsequent to implantation of the implant.

In an application, the apparatus further includes an adjustment-facilitating tool that includes a tensioning element that is reversibly couplable to the pouch, such that while coupled to the pouch, application of a proximally-directed force to the tensioning element stretches the pouch into its stretched state.

In an application, the apparatus further includes a guide member, reversibly coupled to the implant, and the adjustment-facilitating tool is advanceable along the guide member to the implant subsequent to implantation of the implant.

In an application, the adjustment-facilitating tool further includes a pressing element, slidably coupled to the tensioning element such that, while the tensioning element is coupled to the pouch, application of a distally-directed force to the pressing element presses the pressing element against the implant.

In an application, the pressing element maintains coupling between the tensioning element and the pouch, and withdrawal of the pressing element decouples the tensioning element from the pouch.

In an application, the pressing element is disposed coaxially around the tensioning element.

In an application, the tensioning element is disposed coaxially around the pressing element.

In an application, the pressing element is slidably coupled to the tensioning element such that, while the tensioning element is coupled to the pouch, application of the distally-directed force to the pressing element presses the pressing element against the implant body.

In an application, the pressing element is slidably coupled to the tensioning element such that, while the tensioning element is coupled to the pouch, application of the distally-directed force to the pressing element presses the pressing element against the gripper.

In an application, the pressing element is slidably coupled to the tensioning element such that, while the tensioning element is coupled to the pouch, application of the distally-directed force to the pressing element presses the pressing element against an inner surface of the pouch.

In an application, the implant further includes a coupling that is attached to the pouch, and to which the adjustment-facilitating tool is reversibly couplable.

Various methods of using the systems and apparatuses described herein are possible. For example, a method for use with an implant having an implant body and a pouch, can include one or more of the following steps:
implanting the implant in a heart of a subject; and
contracting the implant body by stretching the pouch into a stretched state by pulling on part of the pouch using a tensioning element.

In an application, implanting the implant includes transluminally delivering the implant and anchoring the implant to a valve annulus of the heart, and contracting the implant body includes transluminally contracting the implant.

In an application, implanting the implant includes transluminally delivering a plurality of anchors to the implant, and sequentially driving the anchors through the implant body and into tissue of the heart.

In an application, the implant body can include an annuloplasty ring structure, other annuloplasty device structure, or other cinchable/tensionable structure, and implanting the implant can include anchoring the implant body (e.g., the annuloplasty ring structure, or other structure) to an annulus In an application, contracting the implant body includes stretching the pouch into the stretched state by pulling on the part of the pouch using the tensioning element, while simultaneously providing an opposing force via a pressing element that abuts the implant.

In an application, the method further includes advancing the tensioning element to the implant subsequently to implanting the implant, and prior to contracting the implant.

In an application, advancing the tensioning element to the implant includes advancing the tensioning element over a guide member that is reversibly coupled to the implant.

In an application, the method further includes decoupling the guide member from the implant subsequently to advancing the tensioning element to the implant.

In an application, the method further includes, subsequently to stretching the pouch into the stretched state, allowing the pouch to elastically contract toward a contracted state without reversing the contraction of the implant body.

In an application, the implant includes an elongate member and a gripper, the elongate member extending from the part of the pouch, though the gripper, and into the implant body, and contracting the implant body includes drawing the elongate member through the gripper and into the pouch by stretching the pouch into the stretched state.

In an application, the method further includes, subsequently to stretching the pouch into the stretched state, allowing the pouch to elastically contract toward a contracted state without allowing the elongate member to move back out of the pouch and through the gripper.

In an application, drawing the elongate member through the gripper and into the pouch includes drawing the elongate member through the gripper and into the pouch while maintaining the gripper in an unlocked state.

In an application, the method further includes, subsequently to drawing the elongate member through the gripper and into the pouch, transitioning the gripper into a locked state.

In an application, transitioning the gripper into the locked state includes removing an unlocker from the gripper such that the gripper automatically transitions into the locked state.

Additional components/features and additional steps described elsewhere herein can also be used in the examples above.

The present invention will be more fully understood from the following detailed description of applications thereof, taken together with the drawings, in which:

BRIEF DESCRIPTION OF THE DRAWINGS

FIGS. 1A-C are schematic illustrations of an adjustment system, in accordance with some applications of the invention;

FIGS. 2A-D and 3A-D are schematic illustrations of respective embodiments of an adjustment-facilitating tool being used with the adjustment system to adjust an implant, in accordance with some applications of the invention;

FIGS. 5, 6A-B, and 7A-B are schematic illustrations of respective embodiments of a gripper, in accordance with some applications of the invention.

DETAILED DESCRIPTION OF EMBODIMENTS

Figure 4A:
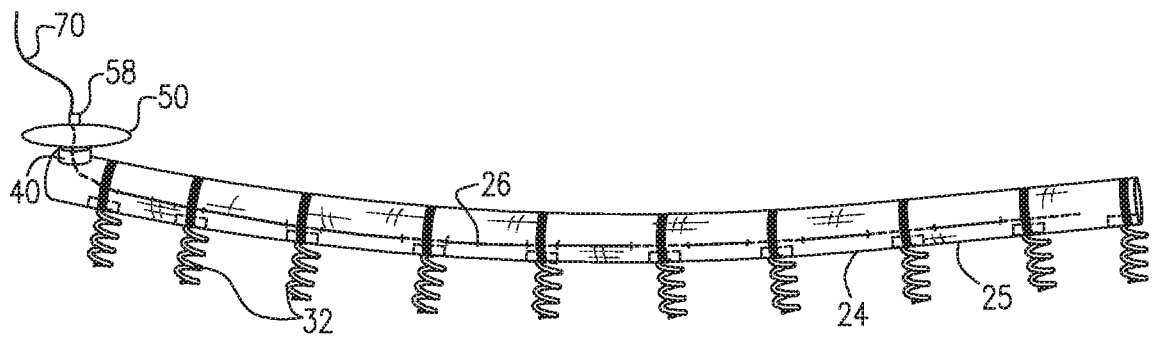
FIGS. 4A-D are schematic illustrations of the use of a guide member to advance the adjustment-facilitating tool to the implant, in accordance with some applications of the invention.
Figure 4B:
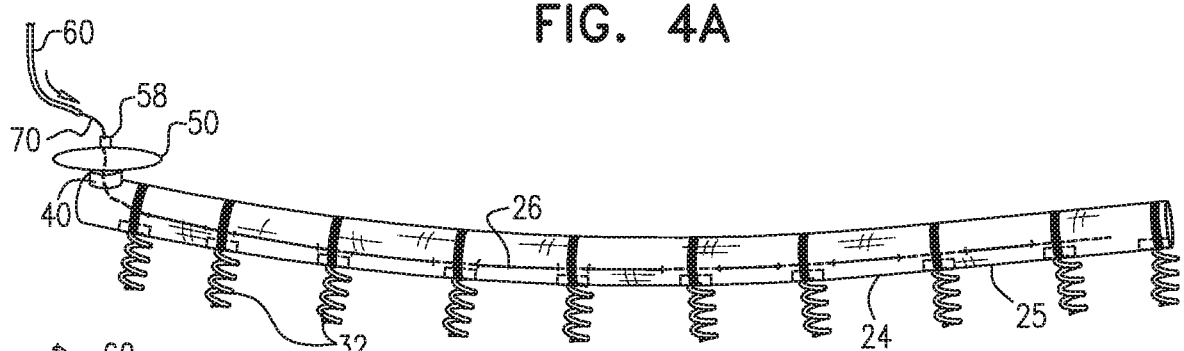

Reference is made to FIGS. 1A-C, which are schematic illustrations of an adjustment system 20, in accordance with some applications of the invention.

System 20 can comprise an implant 22 that comprises an implant body 24, and the system is for adjustment of the implant body. The implant 22 and/or implant body 24 shown can take a variety of forms and those depicted in the various figures herein are merely exemplary. For some applications, and as generally described herein, implant body 24 can be an annuloplasty ring structure, annuloplasty/annulus adjustment structure, other annuloplasty device structure, or other cinchable/tensionable structure. Implant body 24 can comprise a flexible sleeve 25 that has a wall or circumferential wall (e.g., which can be made of a fabric, such as a polyethylene terephthalate fabric, e.g., Dacron™) that circumscribes a longitudinal axis of the sleeve, thereby defining a longitudinal lumen. System 20 (e.g., implant 22 thereof) can further comprise an elongate member 26. Elongate member 26 can comprise one or more strands of metal or polymer, optionally coated with a low-friction coating, such as polytetrafluoroethylene (PTFE). Implant body 24 can be configured to be placed partially or completely around a cardiac valve annulus 10 (e.g., a mitral valve annulus, tricuspid valve annulus, etc.). Implant body 24 can be secured or anchored in place at the valve annulus in a variety of ways, including by suturing the implant body 24 to the valve annulus, e.g., by parachuting similar to a surgical annuloplasty ring or otherwise. Implant body 24 can be configured to be anchored in place using a plurality of (e.g., 5-20) tissue anchors 32. The tissue anchors 32 can have a variety of features, for example, each tissue anchor 32 can comprise a tissue-coupling element 34, and a tool-engaging head 36 fastened to one end of the tissue-coupling element. Following introduction of implant body 24 into the subject, each anchor 32 can be sequentially intracorporeally delivered into the lumen of the sleeve, and its tissue-coupling element 34 can be driven from the interior lumen or from one side through the circumferential wall and into tissue of the valve annulus, thereby anchoring the implant body 24 or sleeve to the valve annulus. After the implant 22 and/or implant body 24 are secured or anchored to the valve annulus, longitudinal contraction of implant body 24, facilitated by system 20, can be used to circumferentially tighten the valve annulus, thereby improving coaptation of the valve leaflets, and reducing regurgitation.

For some applications, the implant structure of implant body 24 can be, or share features with, mutatis mutandis, any of the implant structures described in one or more of the following publications, which are incorporated herein by reference. The relevant features of the system herein may be substituted for adjustment features in these references. For some applications, implant 22 is implanted as described in one or more of these publications, mutatis mutandis:

PCT application publication WO 2010/128503 to Zipory et al.

PCT application publication WO 2012/176195 to Gross et al.

PCT application publication WO 2013/069019 to Sheps et al.

PCT application publication WO 2014/064694 to Sheps et al.

U.S. Pat. No. 8,926,696 to Miller et al.

U.S. Pat. No. 8,353,956 to Miller et al.

FIGS. 1A-C illustrate a generalization of system 20. More specific embodiments are described with reference to later figures.

Implantable apparatus or system 20 can comprise a gripper 40 and a pouch 50 (e.g., an elastic pouch) or other container. Pouch 50 can have a first part 54 and a second part 56, and has a contracted state (see FIGS. 1A and 1C) toward which the pouch is biased (e.g., elastically biased, shape-memory biased, etc.). The pouch 50 can have one or multiple contracted states. In the contracted state, the pouch can be configured to define a contracted distance d1 between the first part and the second part. Pouch 50 can be reversibly stretchable into a stretched state (FIG. 1B) in which the pouch defines a stretched distance d2 between first part 54 and second part 56. Distance d1 is smaller than distance d2. For example, distance d1 may be 1-12 mm (e.g., 1-7 mm, such as 2-6 mm), whereas distance d2 may be 20-100 mm (e.g., 30-80 mm, such as 40-70 mm).

Implantable apparatus or system 20 can also include an elongate member 26 that can extend into the pouch 50. Elongate member can be arranged such that it extends through a gripper 40, and then into pouch 50 via an opening 52. Opening 52 can be defined by second part 56 of the pouch. A first end portion 27 of elongate member 26 can be coupled to implant body 24. A second end portion 29 of elongate member 26 can be fastened to first part 54 of the pouch. Second part 56 can be defined by the location of opening 52, and first part 54 can be defined by the location of the fastening of elongate member 26 to pouch 50.

A third portion or mid-portion 28 of elongate member 26 can be between end portions 27 and 29. Mid-portion or third portion 28 can extend through gripper 40. Gripper 40 is configured (i) to facilitate tensioning of the elongate member, and (ii) to subsequently maintain the tension on the elongate member. As described in more detail hereinbelow, gripper 40 can have at least one state in which third portion or mid-portion 28 is slidable through the gripper and into pouch 50 via opening 52. For example, gripper 40 may facilitate one-way sliding of portion 28 therethrough. Alternatively or additionally, gripper 40 can have (i) an unlocked state in which it facilitates sliding of portion 28 therethrough, and (ii) a locked state in which it inhibits the sliding of the third portion or mid-portion.

Implantable apparatus or system 20 can also comprise an implant 22. FIG. 1A shows implant 22 subsequent to its implantation, and before its adjustment (i.e., contraction). Pouch 50 is shown in a contracted state (e.g., relaxed state). FIG. 1B shows pouch 50 having been reversibly stretched into a stretched state. Because second end portion 29 is fastened to first part 54, this stretching pulls on elongate member 26, drawing it (e.g., third portion or mid-portion 28 thereof) through gripper 40 and opening 52, into pouch 50, thereby longitudinally contracting implant body 24, e.g., by reducing the length of the elongate member disposed within the implant body. For applications in which implant body 24 is an annuloplasty ring structure or other annuloplasty device structure implanted around the valve annulus (e.g., all or a portion thereof), this longitudinal contraction circumferentially tightens the valve annulus, thereby improving coaptation of the valve leaflets, and reducing or eliminating regurgitation. It is to be understood that, during this step, gripper 40 can be in at least one state in which portion 28 is slidable through the gripper and into pouch 50 via opening 52. Optionally, pouch 50 and gripper 40 can be integral with or separate from implant 22. The implants or implant bodies described herein can have an open or closed (e.g., a closed ring) configuration and can be configured for transvascular or transcatheter implantation and/or surgical implantation.

FIG. 1B does not show how pouch 50 is stretched. Some examples of techniques for stretching pouch 50 are described in further detail hereinbelow. However, FIG. 1B does show a coupling 58 via which a tool is couplable to pouch 50 for stretching (e.g., pulling on) the pouch. For some applications, and as shown throughout this patent application, second end portion 29 of elongate member 26 can be fastened to first part 54 of pouch 50 by being fastened to coupling 58. The position of coupling 58 may thereby define or be first part 54 of pouch 50.

Subsequently, pouch 50 is allowed to return toward its contracted state (FIG. 1C), but gripper 40 can be designed or configured to inhibit or prevent elongate member 26 from sliding back through gripper 40 and into implant body 24. For example, and as described hereinbelow, gripper 40 may only facilitate one-way movement of member 26 therethrough, or may have been locked subsequently to the stretching of pouch 50. Because elongate member 26 is inhibited or prevented from sliding back through gripper 40, implant body 24 remains in its reduced length, and the valve annulus remains at its repaired size.

For some applications, pouch 50 can be made from or comprise an elastomer. For some applications, pouch 50 can comprise one or more strands of elastic and/or shape memory material such as Nitinol, e.g., optionally, threaded into the pouch so as to provide the pouch with its elastic nature.

Pouch 50 is typically distinct from an inflatable balloon. For some applications, pouch 50 can be partially permeable, allowing blood (or components thereof) to enter the pouch over time, and facilitating clotting and/or tissue growth therein. It is believed that this may facilitate maintenance of the tension applied to elongate member 26, and thereby maintenance of the contraction of implant body 24.

For some applications, pouch 50 can be impermeable to blood and/or components thereof. It is believed that this may facilitate readjustment of implant 22 subsequent to its implantation and initial contraction.

While a pouch might not be used, the pouch is beneficial to contain and restrict movement of any excess portion of the elongate member. For example, in the absence of pouch 50 (e.g., adjustment by pulling directly on end portion 29), the resulting excess 30 of elongate member 26 outside of implant body 24 may disadvantageously move freely within the body (e.g., within left atrium 6), with potentially deleterious effects. The elastic return of pouch 50 to its contracted state can compress excess 30 of elongate member 26, such that it is tidily confined. It is believed that this can advantageously avoid excess 30 being free within the heart, while obviating a potential need to remove (e.g., by cutting) excess 30.

For some applications, pouch 50, gripper 40, and implant body 24 can be coupled together such that, from proximal end portion 29, until at least implant body 24, elongate member 26 is not exposed to the body of the subject. That is, the pouch and gripper isolate the elongate member from the body of the subject. For some applications, more distal portions of elongate member 26 are exposed to the body of the subject, e.g., if elongate member 26 weaves in and out of implant body 24 (e.g., the circumferential wall of sleeve 25).

Although system 20 is generally described herein as including implant 22, it is to be noted that the scope of the invention does not require the system 20 to include the implant or any other component. For example, system 20 may be provided alone or unattached or uncombined with an implant, such that it can be later attached to and/or used with a different implant, e.g., a third-party implant. In one embodiment, system 20 can comprise pouch 50, gripper 40, elongate member 26, and one or more anchors attached to the elongate member, e.g., without a separate implant body.

Reference is made to FIGS. 2A-D and 3A-D, which are schematic illustrations of exemplary embodiments of adjustment-facilitating tool 60 being used with system 20 to adjust (e.g., contract) implant 22, in accordance with some applications of the invention. Various embodiments of tool 60 can comprise a tensioning element 62, and/or can comprise a pressing element 64.

The use of common reference numerals is intended to indicate commonality between elements of different embodiments, e.g., whereby an element of one embodiment serves the same primary function as the corresponding element of another embodiment. Suffixes (e.g., a, b, etc.) are used to uniquely identify the elements of a particular embodiment. For example, the embodiments of FIGS. 2A-D and 3A-D are depicted as each including a tool 60 (tools 60a and 60b, respectively) that comprises a tensioning element 62 (elements 62a and 62b). Despite the described differences between tools 60a and 60b, and between elements 62a and 62b, both tools are used to contract their respective implant 22, and both tensioning elements are coupled to their respective pouch 50, and are used to apply a proximally-directed force to (i.e., to pull on) the pouch to stretch it.

FIGS. 2A-D show an exemplary embodiment in which a tool 60a (an embodiment of tool 60) comprises a tensioning element 62a (an embodiment of tensioning element 62) and a pressing element 64a (an embodiment of pressing element 64), and an implant 22a (which can be the same as or similar to implant 22 or can be any implant that requires cinching or tightening from a remote or removed location) comprises a gripper 40a (an embodiment of gripper 40), an elastic pouch 50a (an embodiment of pouch 50), and a coupling 58a (an embodiment of coupling 58).

For some applications, implant 22 (e.g., implant 22a) can be delivered and implanted while at least part of tool 60 (e.g., tool 60a) is coupled to the implant. For example, implant 22a can be delivered and implanted while (i) tensioning element 62a is coupled to coupling 58a, and (ii) pressing element 64a abuts implant body 24. Alternatively, implant 22a can be delivered and implanted while (i) tensioning element 62a is coupled to coupling 58a, and (ii) pressing element 64a is proximal to the implant (e.g., within a delivery catheter or outside of the subject), and is subsequently advanced over and along the tensioning element to the implant. Optionally, another arrangement could also be used.

For some applications, implant 22 (e.g., implant 22a) is delivered and implanted without tool 60 (e.g., tool 60b) coupled to the implant, and one or more components of the tool are subsequently advanced to the implant (e.g., over and along a dedicated guide wire or guide member) and coupled to the implant, e.g., as described with reference to FIGS. 4A-D, mutatis mutandis.

While tensioning element 62a is coupled to coupling 58a, the tensioning element can be pulled proximally to reversibly stretch pouch 50a. Stretching the pouch can draw elongate member 26 (e.g., portion 28 thereof) through gripper 40a and into the pouch (FIG. 2B). This can be performed while pressing element 64 provides an opposing force against implant 22 (e.g., against implant body 24) in order that the pulling not pull the implant away from the tissue at which it is implanted. Pressing element 64a can be tubular and/or configured in a variety of shapes. Pressing element 64a can be disposed around tensioning element 62a (e.g., coaxially). Pressing element 64a or at least at its distal end can be wider than pouch 50a, such that it can press against the implant without interfering with the stretching of the pouch. Optionally, the pressing element could be configured to pass to one or more sides of the pouch to contact the implant, e.g., without surrounding the pouch.

After the implant and/or implant body 24 has been sufficiently contracted—which can be determined by imaging of the implant (e.g., using fluoroscopy, etc.), the anatomy, and/or blood flow (e.g., using echocardiography, ultrasound, etc.)—pouch 50a can be allowed to return to its contracted state (FIG. 2C). Gripper 40a can be configured to inhibit elongate member 26 from sliding back through the gripper and into implant body 24. For example, the gripper 40a and/or other grippers described herein can have friction resistance, a latch, valve, clamp, etc. that can allow movement of the member in one direction, but not the other direction. Tool 60a can be decoupled from implant 22a (e.g., element 62a can be decoupled from coupling 58a), and withdrawn from the subject (FIG. 2D). For some applications, and as shown, pouch 50a is allowed to return to its contracted state by moving element 62a distally, and/or by releasing tension on element 62a such that the elastically-contracting pouch pulls element 62a distally. For some applications, pouch 50a is allowed to return to its contracted state by decoupling tool 60a, including moving element 62a, from implant 22a, e.g., skipping the step shown in FIG. 2C.

FIGS. 3A-D show an embodiment in which a tool 60b (an embodiment of tool 60) comprises a tensioning element 62b (an embodiment of tensioning element 62) and a pressing element 64b (an embodiment of pressing element 64), and an implant 22b (e.g., the same as or similar to implant 22, 22a or any implant that needs to be contracted or tensioned) comprises a gripper 40b (an embodiment of gripper 40), an elastic pouch 50b (an embodiment of pouch 50), and a coupling 58b (an embodiment of coupling 58).

For some applications, implant 22b is delivered and implanted while at least part of tool 60b is coupled to the implant. For example, implant 22b can be delivered and implanted while tensioning element 62b is coupled to coupling 58b. Optionally, implant 22a can be delivered and implanted while (i) pressing element 64b is coupled to the implant (e.g., to gripper 40b thereof), and (ii) tensioning element 62b is proximal to the implant (e.g., within a delivery catheter or outside of the subject), and is subsequently advanced over and along the pressing element to the implant.

For some applications, implant 22b is delivered and implanted without tool 60b coupled to the implant, and one or more components of the tool are subsequently advanced to the implant (e.g., over and along a dedicated guide wire or guide member) and coupled to the implant, e.g., as described with reference to FIGS. 4A-D, mutatis mutandis.

While tensioning element 62b is coupled to coupling 58b, the tensioning element can be pulled proximally to reversibly stretch pouch 50b. Stretching pouch 50b can draw elongate member 26 (e.g., portion 28 thereof) through gripper 40b and into the pouch (FIG. 3B). This can be performed while pressing element 64b provides an opposing force against implant 22b in order that the pulling not pull the implant away from the tissue at which it is implanted. In contrast to the arrangement of elements 62a and 64a as shown in FIGS. 2A-2D, tensioning element 62b is depicted as being tubular and disposed around pressing element 64b (e.g., coaxially). Pressing element 64b can be configured and arranged to extend distally from tensioning element 62b, and through pouch 50b, e.g., such that is abuts and presses against the inner surface of the pouch and/or against gripper 40b, and such that it can provide the opposing force without interfering with the stretching of the pouch. Coupling 58b can be shaped to define an opening through which pressing element 64b extends or can extend into pouch 50b. When pouch 50b is stretched, coupling 58b can slide proximally along pressing element 64b.

After the implant 22 and/or implant body 24 has been sufficiently contracted, pouch 50b is allowed to return to its contracted state (FIG. 3C). Gripper 40b can be the same as or similar to other grippers described herein and can be configured to inhibit elongate member 26 from sliding back through the gripper and into implant body 24. Tool 60*b* can be decoupled from implant 22*b* (e.g., element 62*b* can be decoupled from coupling 58*b*), and withdrawn from the subject (FIG. 3D). For some applications, and as shown, pouch 50*b* can be allowed to return to its contracted state by moving element 62*b* distally, and/or by releasing tension on element 62*b* such that the elastically-contracting pouch pulls element 62*b* distally. For some applications, pouch 50*b* is allowed to return to its contracted state by decoupling tool 60*b*, including element 62*b*, from implant 22*b*, e.g., skipping the step shown in FIG. 3C.

For some applications, pressing element 64 maintains the coupling between tensioning element 62 and coupling 58. For example, with reference to FIGS. 3A-D, the presence of pressing element 64*b* within coupling 58*b* may hold a detent 66 defined by tensioning element 62*b* within a recess 68 defined by coupling 58*b* (or a detent defined by the coupling within a recess defined by the tensioning element). For example, the pressing element and/or detent can be configured or designed such that, upon removal of the pressing element, the detent automatically retracts from the recess, decoupling the tensioning element from the coupling.

Reference is again made to FIGS. 2A-D and 3A-D. Optionally, tool 60 can comprise an extracorporeal controller (not shown), which can comprise at least one handle, at the proximal end of elements 62 and 64. For some applications, the length of elongate member 26 (e.g., of portion or mid-portion 28) that slides proximally through gripper 40 and into pouch 50 is proportional (e.g., equal) to the amount by which implant body 24 contracts. Therefore, for some applications, the length by which implant body 24 contracts can be proportional (e.g., equal) to the distance moved by tensioning element 62 relative to pressing element 64. For some such applications, the amount of contraction of implant body 24 can be indicated by control members of the extracorporeal controller. For example, actuation of a control member (e.g., turning of one or more knobs) may cause movement between elements 62 and 64, and the amount that the control member has been actuated (e.g., the amount that the one or more knobs have been turned) can be indicated by a dial. For example, thereby indicating the amount of relative movement between elements 62 and 64, and thereby the amount of contraction of implant body 24.

Figure 4C:
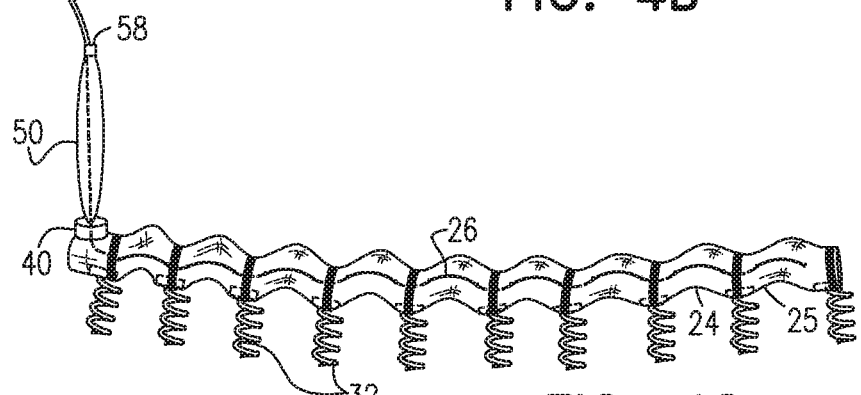
Figure 4D:
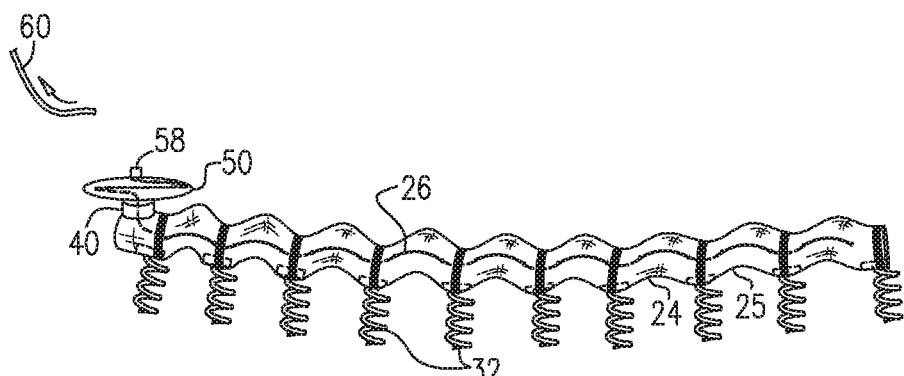

Reference is now made to FIGS. 4A-D, which are schematic illustrations of the use of a guide member 70 (e.g., which can be a guide wire or other guide) to advance adjustment-facilitating tool 60 to implant 22 and/or to pouch 50, in accordance with some applications of the invention. For some applications, the implant can be implanted without an adjustment tool (e.g., tool 60) coupled thereto, and the tool can be subsequently advanced to the implant in order to adjust the implant. For such applications, implant 22 can be implanted with a guide member 70 coupled thereto (FIG. 4A). Subsequent to implantation, tool 60 can be advanced along (optionally over) guide member 70 (FIG. 4B), then tensioning element 62 can be coupled to pouch 50 (e.g., via coupling 58). Tool 60 can then be used to adjust implant 22 (e.g., to longitudinally contract the implant), e.g., by reversibly stretching pouch 50 (FIG. 4C). Pouch 50 can then be allowed to return to its contracted state, and tool 60 can be decoupled from implant 22 (FIG. 4D). As shown, guide member 70 can be decoupled from implant 22 subsequent to adjustment of the implant. This can be achieved by any suitable technique, such as unscrewing, unlocking a lock, etc., and can be performed using tool 60.

For some applications, guide member 70 is coupled to implant 22 at coupling 58. For some applications, guide member 70 is coupled to implant 22 at gripper 40 (e.g., as described with reference to FIGS. 6A-B). For some such applications, guide member 70 extends through pouch 50 to gripper 40. Other coupling options are also possible.

Reference is now made to FIGS. 5, 6A-B, and 7A-B which are schematic illustrations of exemplary embodiments of gripper 40. As described hereinabove, gripper 40 can allow for unidirectional movement/sliding or have at least one state in which third portion or mid-portion 28 of elongate member 26 is slidable through the gripper and into pouch 50 via opening 52. The gripper 40 can be configured such that the portion 28 and/or elongate member 26 is not slidable from the pouch back in to the implant. For example, gripper 40 may facilitate only one-way sliding of portion 28 therethrough. Optionally, it is also possible to configure gripper 40 to allow movement or sliding of the portion 28 and/or elongate member 26 into and out of the gripper 40 in both directions until the gripper is locked, clamped, or otherwise secured to prevent movement or sliding of the portion 28 and/or elongate member 26 therethrough. For example, gripper 40 may have (i) an unlocked state in which it facilitates sliding of portion 28 therethrough, and (ii) a locked state in which it inhibits the sliding of the portion/mid-portion.

FIG. 5 shows an exemplary embodiment 80 of gripper 40, which has a unidirectional state in which the gripper facilitates one-way sliding of portion 28 therethrough. Gripper 80 can comprise one or more wheels 82, each wheel comprising a gripping surface 84 (e.g., comprising a plurality of teeth or comprising other frictional element(s)) that can grip portion 28. Wheels 82 can be configured to rotate in only one rotational direction, and thereby facilitate movement of portion 28 in a first direction through the gripper into pouch 50, but not in a second direction through the gripper out of the pouch. For example, gripper 80 may comprise a pawl 86 that allows rotation of wheel 82 in only one rotational direction. Optionally, the one or more wheels could be configured to allow rotation in both directions until locked or secured to prevent further movement.

Figure 6A:
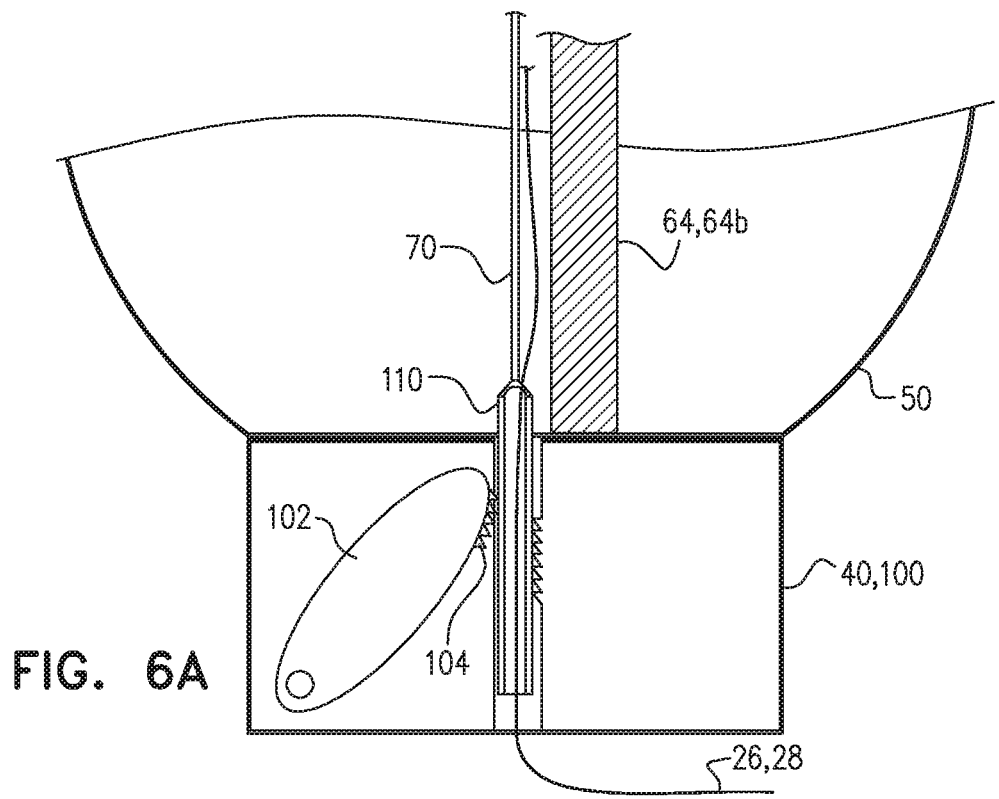
Figure 6B:
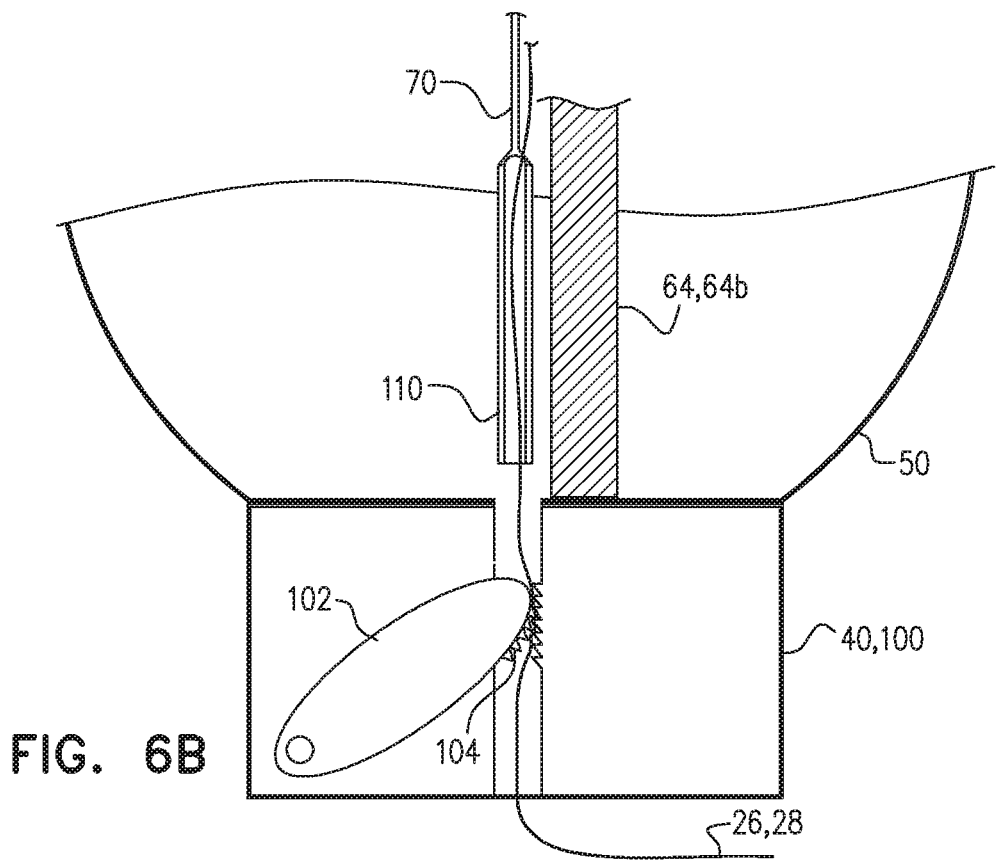

FIGS. 6A and 6B show an exemplary embodiment 100 of gripper 40 in which the gripper has (i) an unlocked state in which it facilitates sliding of portion 28 in either direction therethrough, and (ii) a locked state in which it inhibits the sliding of the portion in either direction. Optionally, the gripper can be biased to assume the locked state.

For some applications, gripper 100 can comprise at least one locking element 102 (e.g., a jaw, latch, contact edge, etc.) that, in the locked state, clamps onto portion 28 or elongate member 26. The jaw 102 (or other locking element) can have a gripping surface 104, such as one or more teeth or other frictional feature(s), that frictionally engages or grips portion 28 when the locking element or jaw contacts or clamps onto the portion of elongate member 26.

The system can also comprise an unlocker 110, which can be configured to maintain the gripper in an unlocked state. Optionally, gripper 100 can be configured to automatically transition into a locked state upon removal of unlocker 110 from the gripper. As shown, for example, in FIGS. 6A and 6B, unlocker 110 can be shaped to define a partial tube that inhibits (e.g., obstructs) jaw 102 (or other locking element) from clamping on to portion 28 and allows the portion to slide through the cavity defined by the partial tube. Because the unlocker defines only a partial tube, it is not threaded onto elongate member 26, and can therefore be removed from the implant after the gripper is locked. Unlocker 110 thereby serves as an actuator of gripper 100 (e.g., of jaw 102 thereof), via which the gripper is transitionable between its unlocked and locked states.

For some applications, and as shown, unlocker 110 can be defined by, or can be coupled to, the distal end of guide member 70. For such applications, guide member 70 can continue distally past coupling 58 and into pouch 50. Optionally, unlocker 110 can be distinct from guide member 70, and/or can be used in systems that do not include guide member 70.

Figure 7A:
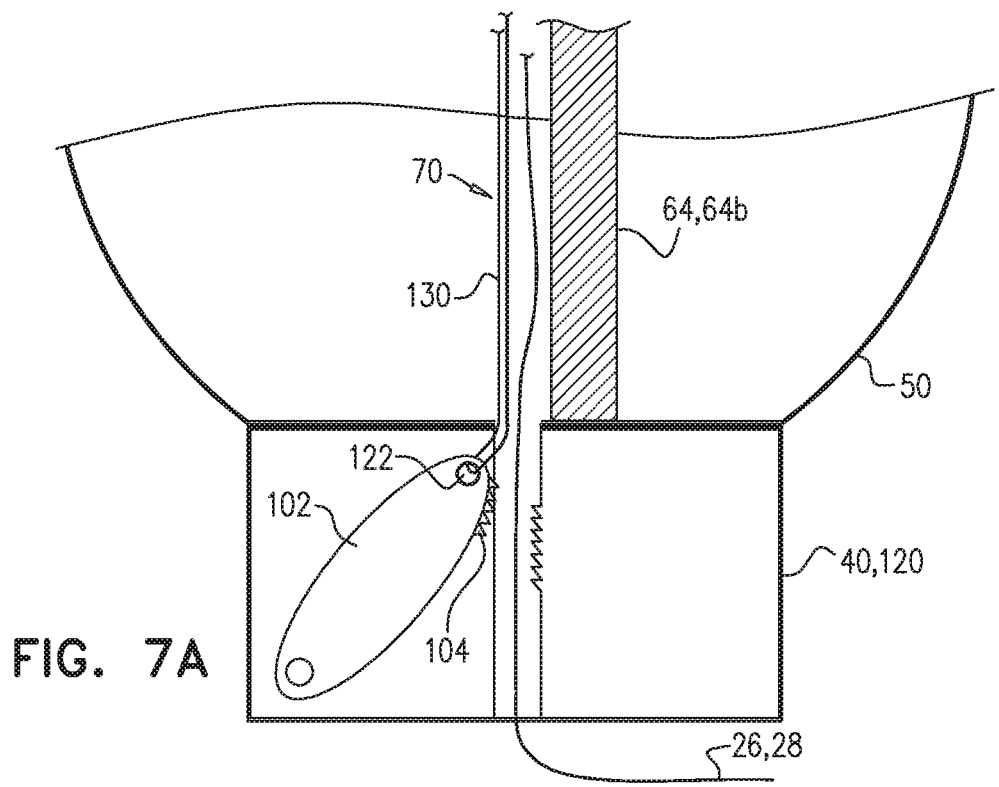
Figure 7B:
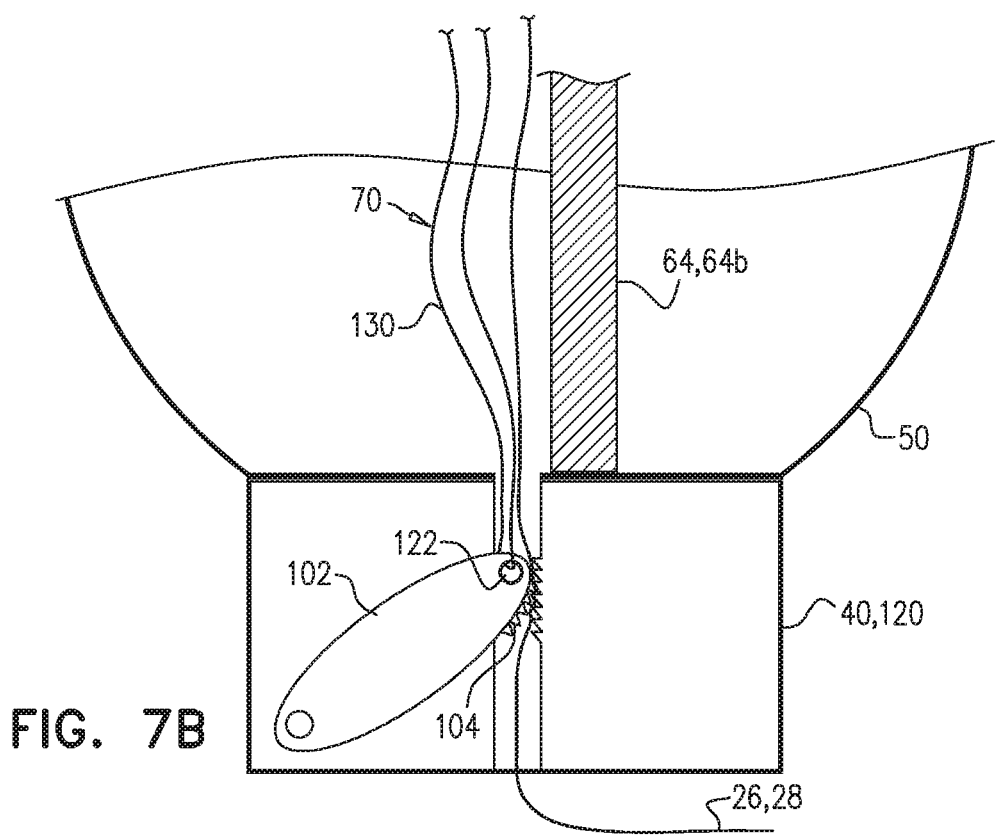

FIGS. 7A and 7B show another exemplary embodiment 120 of gripper 40 in which the gripper has (i) an unlocked state in which it facilitates sliding of portion 28 in either direction therethrough, and (ii) a locked state in which it inhibits the sliding of the portion in either direction. Gripper 120 is typically identical to gripper 100 except where noted.

Gripper 120 is configured to be transitioned between its locked and unlocked states via an unlocker 130, which thereby serves as an actuator of gripper 120 (e.g., of jaw 102 thereof). In contrast to unlocker 110, unlocker 130 actuates gripper 120 by pulling on jaw 102, thereby pulling the jaw away from mid-portion 28 of elongate member 26. Unlocker 130 is reversibly coupled to jaw 102, such that when the unlocker is pulled proximally (e.g., tensioned), the jaw is opened, thereby transitioning the gripper into its unlocked state. The gripper can be biased to assume the locked state (e.g., in the absence of pulling by unlocker 130).

For some applications, and as shown, unlocker 130 comprises a filament (e.g., a wire or suture), and is reversibly coupled to jaw 102 by being looped around part of the jaw. For example, and as shown, the filament may be coupled to the jaw by being looped through an eyelet 122 that is coupled to or defined by the jaw. For some such applications, both ends of the filament are disposed outside of the heart (e.g., outside of the subject), and the unlocker is tensioned by pulling on both ends. For some such applications, decoupling of the unlocker from the gripper is achieved by releasing one end of the filament and pulling on the other end of the filament, causing the released end to travel toward the jaw and through the eyelet, thereby unthreading the filament from the eyelet.

For some applications, and as shown, unlocker 130 (e.g., proximal portions thereof) also serve as guide member 70, e.g., as described hereinabove, mutatis mutandis. This may alternatively be viewed as the unlocker being defined at a distal end of the guide member.

The use of unlocker 130 allows gripper 120 to be reversibly locked (e.g., locked, unlocked, and relocked), thereby further facilitating controlled contraction of the implant.

Other grippers described or shown herein can also include an unlocker, for example, gripper 80 can also have an unlocked state, and can be provided with an unlocker that inhibits wheels 82 from engaging portion 28 in one position and can be moved to another position to allow wheels 82 to engage portion 28.

The gripper 40 is not limited to what has been particularly shown and described hereinabove. For example, although gripping surfaces 84 and 104 are both shown as comprising teeth, other gripping surfaces (e.g., high friction surfaces) may be used. For some applications, the gripper can comprise a radially-contracting element (e.g., a helical spring) that is configured to grip the elongate member by being biased to radially contract, e.g., upon removal of an unlocker.

Grippers 40, 80, 100, and 120 etc. can be used in combination with any of the implants described herein, mutatis mutandis. For example, gripper 40*a* of implant 22*a*, or gripper 40*b* of implant 22*b*, can comprise gripper 80, 100, 120, or another gripper, mutatis mutandis. The grippers may alternatively or additionally be used to facilitate tensioning of, and/or maintenance of tension on, elongate members of other implants, including implants that do not comprise pouch 50. Such implants include adjustable annuloplasty bands, adjustable annuloplasty rings, and adjustable prosthetic chordae tendineae.

The present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description. Methods can include steps described above in various orders and combinations. Features and characteristics of one embodiment can be combined or incorporated into other embodiments.

The invention claimed is:

1. A system comprising:
    an implant body;
    a gripper having at least one state;
    an elastic pouch:
        having a first part and a second part, the first part being coupled to the gripper,
        stretchable into a stretched state in which the pouch defines a stretched distance between the first part and the second part, and
        having a contracted state toward which the pouch is elastically biased, and in which the pouch defines a contracted distance between the first part and the second part, the contracted distance being smaller than the stretched distance; and
    an elongate member, wherein the elongate member extends along the implant body and at least a first portion of the elongate member is coupled to the implant body;
    wherein, in the at least one state of the gripper, at least a second portion of the elongate member is slidable through the gripper and into the pouch; and
    wherein the implant body, elongate member, and the pouch are configured such that stretching the pouch into the stretched state longitudinally contracts the implant body.

2. The system according to claim 1, wherein the elongate member has an end portion that is fastened to the second part of the pouch, such that, in at least the one state of the gripper, stretching of the pouch into the stretched state pulls the elongate member through the gripper and into the pouch.

3. The system according to claim 1, wherein the first part of the pouch defines an opening into the pouch, and wherein in the at least one state of the gripper, the elongate member is slidable through the gripper and into the pouch via the opening.

4. The system according to claim 1, wherein the at least one state of the gripper includes a unidirectional state in which the gripper facilitates sliding of the elongate member through the gripper in a first direction that is into the pouch, and inhibits sliding of the elongate member through the gripper in a second, opposite direction that is out of the pouch.

5. The system according to claim 4, wherein the gripper has an unlocked state in which the gripper facilitates sliding of the elongate member through the gripper in the first direction and in the second direction.

6. The system according to claim 4, wherein the gripper comprises one or more wheels that, in the unidirectional state, grip the elongate member, each of the one or more wheels configured to rotate in only one rotational direction.

7. The system according to claim 1, wherein the at least one state of the gripper includes:
an unlocked state in which the gripper facilitates sliding of the elongate member through the gripper in a first direction that is into the pouch, and in a second, opposite direction that is out of the pouch, and
a locked state in which the gripper inhibits sliding of the elongate member through the gripper in the first direction and in the second direction.

8. The system according to claim 7, further comprising an unlocker, configured to maintain the gripper in the unlocked state, the gripper configured to automatically transition into the locked state upon removal of the unlocker from the gripper.

9. The system according to claim 8, wherein the gripper comprises a jaw that, in the locked state, clamps onto the elongate member, and the unlocker maintains the gripper in the unlocked state by inhibiting the jaw from clamping onto the elongate member.

10. The system according to claim 8, wherein:
the system further comprises an implant and further comprises a guide member that defines the unlocker at a distal end of the guide member,
the system further comprises an adjustment-facilitating tool that comprises a tensioning element that is reversibly couplable to the pouch, such that while coupled to the pouch, application of a proximally-directed force to the tensioning element stretches the pouch into its stretched state, and
the adjustment-facilitating tool is advanceable along the guide member to the implant subsequent to implantation of the implant.

11. The system according to claim 1, further comprising an adjustment-facilitating tool that comprises a tensioning element that is reversibly couplable to the pouch, such that while coupled to the pouch, application of a proximally-directed force to the tensioning element stretches the pouch into its stretched state.

12. The system according to claim 11, further comprising a guide member, reversibly coupled to the implant, wherein the adjustment-facilitating tool is advanceable along the guide member to the implant subsequent to implantation of the implant.

13. The system according to claim 11, wherein the adjustment-facilitating tool further comprises a pressing element, slidably coupled to the tensioning element such that, while the tensioning element is coupled to the pouch, application of a distally-directed force to the pressing element presses the pressing element against the implant.

14. The system according to claim 13, wherein the pressing element maintains coupling between the tensioning element and the pouch, and withdrawal of the pressing element decouples the tensioning element from the pouch.

15. The system according to claim 13, wherein the pressing element is slidably coupled to the tensioning element such that, while the tensioning element is coupled to the pouch, application of the distally-directed force to the pressing element presses the pressing element against the gripper.

16. The system according to claim 1, wherein the implant body comprises a fabric sleeve that defines a circumferential wall that defines a lumen.

17. The system according to claim 16, further comprising a plurality of anchors, wherein each anchor of the plurality of anchors:
comprises a tissue-coupling element and a tool-engaging head fastened to one end of the tissue-coupling element, and
is configured to be intracorporeally delivered into the lumen of the sleeve, and to anchor the sleeve to the tissue of the subject by the tissue-coupling element being driven through the circumferential wall and into the tissue.

18. The system according to claim 8, wherein the unlocker comprises a filament, reversibly coupled to the unlocker, and wherein tensioning of the filament transitions the gripper to the unlocked state.

19. The system according to claim 8, wherein:
the gripper comprises a jaw that, in the locked state, clamps onto the elongate member, and
the unlocker comprises a filament, reversibly coupled to the jaw such that tensioning of the filament can transition the gripper into the unlocked state by pulling the jaw away from the elongate member and into the locked state by reducing tension on the filament.

* * * * *